United States Patent [19]

Ponnet

[11] Patent Number: 5,151,315
[45] Date of Patent: Sep. 29, 1992

[54] COMPOSITE MATERIAL FOR MEDICAL OR PARAMEDICAL PARTICULARLY ORTHOPAEDIC USE AND METHOD FOR MANUFACTURING IT

[76] Inventor: Tom P. M. G. Ponnet, Lode Vissenaekenstraat 2, B -2600 Berchem, Belgium

[21] Appl. No.: 715,322

[22] Filed: Jun. 14, 1991

Related U.S. Application Data

[63] Continuation of Ser. No. 338,505, Apr. 12, 1989, abandoned, which is a continuation-in-part of Ser. No. 104,065, Oct. 5, 1987, abandoned.

[30] Foreign Application Priority Data

Oct. 8, 1986 [BE] Belgium .............................. 2/61067
Nov. 21, 1986 [BE] Belgium .............................. 2/61090
Dec. 19, 1986 [BE] Belgium .............................. 2/61130

[51] Int. Cl.⁵ .............................................. B32B 7/02
[52] U.S. Cl. .................................. 428/212; 428/137;
428/138; 428/213; 428/215; 428/518.4;
428/318.6; 428/316.6; 428/317.3; 428/319.3;
428/319.7; 428/319.9; 428/402; 428/402.24;
428/325; 428/331; 428/423.7; 428/425.9;
428/524; 428/480; 428/425.3; 428/423.3

[58] Field of Search .................. 428/137, 317.9, 318.4,
428/423.3, 212, 316.6, 318.6, 318.8, 423.5, 402,
402.24, 319.3, 325, 331, 339, 423.7, 524, 525,
425.3, 480, 138, 213, 215, 207, 425.9, 319.7,
319.9, 316.6, 317.3; 128/90

[56] References Cited

U.S. PATENT DOCUMENTS 3,314,419 4/1967 Quick ..................................... 128/90
3,692,023 9/1972 Phillips et al. ......................... 128/90
3,728,206 4/1973 Buese ................................... 428/138
3,915,923 10/1975 Ward ...................................... 528/65

FOREIGN PATENT DOCUMENTS 905981 7/1987 Belgium .
2507829 9/1976 Fed. Rep. of Germany .
2519992 7/1983 France .
2015004 9/1979 United Kingdom .

Primary Examiner—Ellis P. Robinson
Assistant Examiner—Donald J. Loney
Attorney, Agent, or Firm—Stevens, Davis, Miller & Mosher

[57] ABSTRACT

The composite material comprises a core of a thermoplastic composition containing 20 to 70 weight % caprolactone polyester polyurethane and 80 to 30 weight % polycaprolactone, and a coating of open-cell polyurethane foam with a thickness between 0.5 and 1.5 mm on each side of the core. The core may consist of three layers, the middle one having a lower caprolactone content than the others, and may comprise 1 to 40 weight % glass microspheres and a coloring agent.

12 Claims, 2 Drawing Sheets

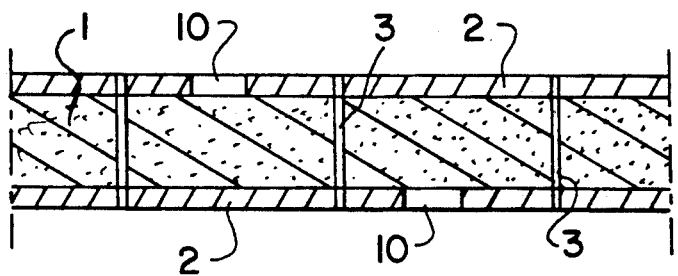
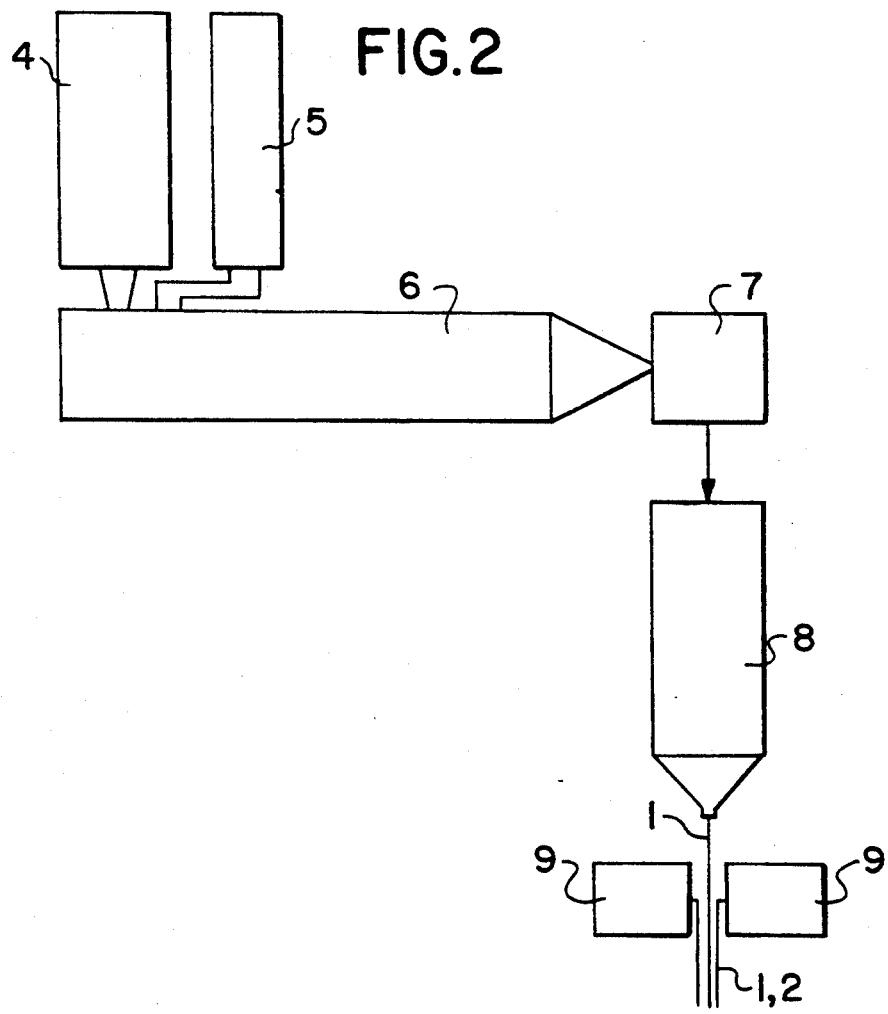

COMPOSITE MATERIAL FOR MEDICAL OR PARAMEDICAL PARTICULARLY ORTHOPAEDIC USE AND METHOD FOR MANUFACTURING IT

This application is a continuation of application Ser. No. 338,505, filed Apr. 12, 1989, now abandoned, which is a continuation-in-part of application Ser. No. 104,065, filed Oct. 5, 1987, is now abandoned.

BACKGROUND OF THE INVENTION

The invention relates to a composite material for medical or paramedical, particularly orthopaedic use, which comprises a thermoplastic composition based on polycaprolactone and polyurethane.

A thermoplastic composition based on polycaprolactone and polyurethane is known from EP-A-0 087 329.

The polyurethane is formed in situ in soft form in the polycaprolactone from a polyol and at least one polyisocyanate.

The resulting polycaprolactone-polyurethane composition is manufactured in the shape of plates or sheets, and it is being used as such to replace plaster bandages.

The composition is made soft and self-adhesive by heating same above 60° C., by dipping into hot water, and thereafter is put in the desired shape on the body. Parts of the material are stuck to one another. After cooling, the material forms a rigid unit.

The arrangement in position of such material is however not easy because it is highly self-adhesive in plastic condition. Once portions thereof have been brought against one another, it is substantially impossible to release these portions thereafter. It is therefore not possible to present a strip of this material in the form of a roll, unless a sheet is intercalated between the windings to prevent sticking the windings together. Correcting faults when applying the material is also impossible in practice. However, the material cools very fast, in such a way that it also becomes rigid again quite fast and the time interval during which said material can be applied in position is limited.

The composite material is also in direct contact with the body. This may not only cause allergic reactions due to chemicals possibly still present in the material, but it is mostly uncomfortable due to the relatively high temperature at the beginning of the application. Due to direct contact of the material with the skin, breathing through the skin is hampered.

There is known from U.S. Pat. No. 3,728,206, a material based on polyurethane and polycaprolactone, but such material is formed by impregnating a single layer of non-thermoplastic polyurethane foam with a caprolactone for example.

Said material which is also used for replacing plaster bandages is softened by heating above 49° C., preferably above 82° C.

It is however so strongly adhesive that it is generally protected with a coating, for example an aluminum foil. When said material is handled in rolls, it is coated on one side with silicone-processed paper to prevent the windings sticking to one another.

The requirement of having to remove such protection when using the material makes the application thereof difficult. The material is not self-supporting. A spool has to be used to support the roll windings.

Moreover with this material also, no correction is possible any more once portions of the material in plastic condition have contacted one another. Releasing such portions is substantially impossible due to inadvertently sticking together of the strips of the material and the impossibility to release the parts stuck together, winding the material around moving body parts, is nearly impossible. The person applying the material has to wear gloves.

Direct contact of the material with the skin should further be avoided, on the one hand possibly because of the relatively high temperature which is required to make the material plastic and workable, and on the other hand to prevent the action of possible chemicals on the skin. This is the reason why according to the American patent, the material is not laid directly on the body, but an orthopaedic stocking is first put on. Thereby the drawbacks of the direct contact are indeed avoided and the skin can breathe, but the orthopaedic stocking is relatively costly and the requirement of such a stocking makes the application of the orthopaedic bandage time-consuming and more difficult.

The invention has for object to obviate said drawbacks and to provide a composite material for medical or paramedical, particularly orthopaedic use, the use of which is very simple and unexpensive and notably plastic portions of which brought against one another, may be released again, which composite material can be applied directly on the skin without danger or uncomfortable feeling and lets the skin breathe, in such a way that the use of orthopaedic stockings or similar protections between the skin and the material is superfluous.

THE INVENTION

For this purpose, a core of the thermoplastic composition is provided on both sides with a coating of foam plastic material.

The thermoplastic composition contains 20 to 70 weight % polyurethane and 20 to 30 weight % polycaprolactone.

The core has a thickness between 0.05 and 25 mm. The foam plastic is a soft non-thermoplastic resilient, open cell plastic material which withstands temperatures at which the thermoplastic material is softened or weakened.

The layer or coating may be partly penetrated in the core but its thickness outside the core lies between 0.05 and 1.5 mm. The plastic foam forms an insulating layer which avoids the weakened thermoplastic composition contacting directly the skin, delays the composition cooling and lets the skin breath. The foam plastic, outside the core is before the application in no way filled with thermoplastic material as for example the foam plastic from the composite material according to U.S. Pat. No. 3,728,206 which foam plastic does not form a coating.

According to the invention, the foam plastic forms a coating which prevents portions of the composite material from sticking inadvertently to one another. On the one hand, by exerting a small press overlapping portions of the weakened thermoplastic composition may still stick to one another through the foam plastic coating, as the composition squeezes through the plastic foam, but on the other hand due to the presence of the plastic foam, such portions sticking to one another may still be released as long as the composition is in weakened condition.

In this embodiment, the material may be laid with whatever side against the skin. Gripping the material with bare hands can be done. After some time and certainly after the thermoplastic material has set, the portions adhere very strongly to one another.

Layers of plastic foam with a thickness outside of the core of more than 1.5 mm would not let through the thermoplastic core material and prevent a good adherence between overlapping parts of the composite material.

In an advantageous embodiment of the invention, the foam plastic coating is provided with perforations.

In another advantageous embodiment of the invention, the composite material is provided with perforations cross-wise through the core and coating.

In a particularly useful embodiment of the invention, the polyurethane in the thermoplastic composition is a caprolactone polyester polyurethane.

In a remarkable embodiment of the invention, the layer of the thermoplastic composition is manufactured starting from a mixture of a polycaprolactone granulate and a polyurethane granulate.

As opposed to the teaching in EP-A-0 087 329, it appears that according to the invention, the polyurethane does not necessarily have to be formed in soft condition in the polycaprolactone.

When one starts with granulates of polycaprolactone and polyurethane, there is obtained according to the invention a composite material which still has sufficient mechanical properties.

Another aim of the invention is to provide a composite material in the above mentioned kind with a reduced heating up time before it can be applied.

For this purpose the core of thermoplastic material is provided on both sides with said coating of foam plastic material and is comprised of three layers, a middle layer containing 20 to 70 weight % polyurethane and 80 to 30 weight % polycaprolactone, and two outer layers containing a higher polycaprolactone content and having a lower weakening point than said middle layer.

Still another aim of the invention is to provide a composite material of the above mentioned kind having a slower cooling and especially suited for heating-up in a micro-wave oven.

For this purpose, the core of said thermoplastic composition provided on both sides with a coating of said foam plastic material, comprises 1 to 40 weight % of microspheres of non-metallic, heat-accumulating material.

Especially suited are glass microspheres with a diameter between 20 to 800 micrometer. Usefully a coloring agent can be added to the layer comprising microspheres.

Other features and advantages of the invention will stand out from the following description of a composite material for medical or paramedical, particularly orthopaedic use, and of a method for manufacturing such a composite material, according to the invention; said description is only given by way of example and does not limit the invention; the reference numerals pertain to the accompanying drawings.

DRAWINGS

FIG. 1 shows a cross-section of part of a composite material according to the invention.

FIG. 2 shows a block diagram of a method for manufacturing said composite material.

DESCRIPTION OF PREFERRED EMBODIMENTS

Figure 3:
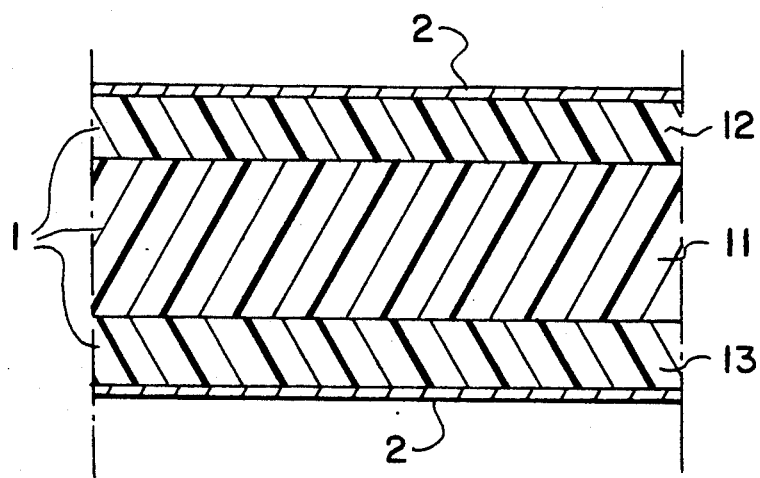
FIG. 3 shows a cross-section similar to that of FIG. 1 of a composition material according to the invention, but relating to another form of embodiment. In the different drawings the same numerals refer to similar elements.

The composite material as shown in FIG. 1 is comprised of a core 1 from a thermoplastic composition comprised of 20 to 70 weight- % and preferably 50 to 60, for example 55 weight- % polyurethane, and 80 to 30 weight- % and preferably 50 to 40 weight- %, for example 45 weight- % polycaprolactone, and on either side of said core, a foam plastic coating 2.

The molecular weight of the polyurethane preferably lies between 10,000 and 100,000, and the molecular weight of the polycaprolactone preferably lies between 10,000 and 60,000, in particular preferably between 37,000 and 50,000.

Polyester polyurethanes are mostly suitable as polyurethane.

Caprolactone polyester polyurethane is particularly suitable, which polyurethane may be obtained by reacting isocyanate and polycaprolactone-based polyester.

Such a caprolactone polyester polyurethane is put on the market as a granulate by B. F. Goodrich Belgium under the name Gamma Estane ®, type 5720.

The melting point of said polycaprolactone polyester polyurethane lies between 190° and 210° C. By adding the polycaprolactone, also preferably in granulate form, there is obtained a thermoplastic composition which is already distortable and kneadable at a temperature of 69° C., and remains distortable by cooling down to about 50° C.

At this temperature, the core 1 of said material can be stretched at least up to twenty times the original length thereof.

In cold condition, the thermoplastic composition is relatively rigid.

The thickness of core 1 normally lies between 0.5 and 25 mm.

The coatings 2 to the contrary are markedly thinner. They have a thickness between 0.05 and 1.5 mm that preferably amounts to about 0.6 mm and are from so-called soft plastic open cell foam.

When the composite material is presented in the shape of a roll, the maximum thickness of the foam layer is preferably of 0.6 mm and when the material is used as a small strip for winding around body parts the thickness of the foam layer is preferably not higher than 0.4 mm. The foam should have such open-cell structure that core material in softened condition can traverse it when pressure is exerted but also that the layer can be elastically deformed without tearing. When the composite material is heated up, it can be stretched up to four times its original length.

Suitable foam plastics for the coatings 2 are polyurethane, particularly polyester polyurethane, and polyether foam.

For some applications, one or both coatings 2 may be provided with perforations 10 with a diameter of at least 0.5 mm and for example 2 mm. Such perforations are for example required when heating the composite material occurs in a warm water bath. The plastic foam absorbes water. Even after squeezing the water out of the plastic foam, there still remains a water fraction which opposes sticking. In the location of part at least of the perforations there is no water, and the plastic from core 1 of one layer can contact the plastic from the core 1 of an above-lying layer.

Cross-wise through core 1 and coatings 2, generally smaller perforations 3 with a diameter of at least 0.5 mm and preferably about 1 to 1.3 mm may be provided, so as not to hamper the skin breathing after applying the material. Said perforations 3 lie on rows crossing each other under 90° and making an angle of 45° with the transversal direction of the strip, plate or roll of composite material, at a distance from each other in the rows of 1.5 to 4 mm.

As shown in FIG. 2, the composite material may be manufactured by feeding a polycaprolactone granulate from a supply bin 4 and a polyurethane granulate from a supply bin 5, to a twin screw extruder. During the extrusion, the granulates are mixed and under the action of pressure and possibly heat, they become fluid. A string of the polyurethane-polycaprolactone composition is pressed out of extruder 6. Said string is fed to the chopper 7 where it is chopped into small pieces. In this way, new granulates are obtained from the thermoplastic composition of polycaprolactone and polyurethane.

Immediately thereafter or some time later, said granulates are again fed to a second extruding device 8, whereby thus the thermoplastic composition is extruded in the form of a layer which comprises the core 1.

By means of foam sprayers 9, a coating 2 of foam plastic is finally sprayed over both sides of core 1.

It is naturally also Possible to manufacture the coatings 2 separately in the form of foam plastic layers and thereafter to apply same on the adhesive layer which comes out of extruding device 8.

Said last way is appropriate when the coatings 2 only are provided with perforations 10. The perforations may be made in the coatings 2 before said coatings are applied on core 1. When the perforations 3 have to extend through the coatings 2 and core 1, said perforations 3 may naturally be made after applying the coatings 2 on core 1.

Due to the presence of coatings 2 of plastic foam, the composite material may be applied directly in distortable condition on the skin. It does not stick to hair and skin. It is soft to the touch. It does not either leave visible fingerprints, so that throw-away gloves do not have to be used for the application. It does let X-rays well through.

Portions of the composite material 1,2 which are brought one against the other, for example the ends of a strip of such material, adhere in the plastic condition of core, 1, sufficiently to one another to remain sticking to one another, but not so strongly that they can not be released any more from one another. The core portions always adhere through two thin layers of coating 2. After some time however, under the action of the pressure from the above-lying material portion, the distortable plastic squeezes through the thin layers of coating 2 and after cooling, the portions strongly stick to one another. After being heated again, the portions may however be pulled away again from one another.

When applying the composite material, corrections may thus easily be made and a piece from the composite material may also be used anew a plurality of times.

Possible residues from the material are also not lost. A plurality of material layers may be laid over one another in plasticized condition.

As the coatings 2 form a thin insulating layer, the working time in the plasticized condition of core 1, is relatively long. Moreover, the skin is subjected to little trouble from the relatively high temperature which is required to make the core 1 plastic and distortable.

The skin may still breathe even after application of the material.

Heating the material to plasticize the core preferably occurs in dry condition, for example by means of hot air, or in a microwave oven, although heating in a liquid is possible. In this latter case, the liquid has to be pressed out of the foam plastic coating before making use of the composite material.

The composite material is relatively homogeneous, does not crumble and is simple to work with, wear-resistant, withstands chemicals and ageing processes, and is impact-resistant.

The composite material is thus particularly suitable for replacing plaster bandages, splints or similar.

The invention will be further explained with reference to the following examples.

EXAMPLE 1

A mixture of 50 weight- % polycaprolactone and 50 weight- % caprolactone polyester polyurethane obtained by reacting isocyanate and a polycaprolactone-based polyester, in the shape of granulates, is regranulated and extruded in the form of a strip with a thickness of 1.4 mm maximum and 0.5 mm minimum. Said strip is coated on both sides thereof with a coating 2 of polyester polyurethane foam with 0.6 mm thickness, which is provided with perforations 10 with a diameter of at least 0.5 mm, which take up a total surface area of 40 % at the most of the coating.

After such shaping, the strip of composite material is further provided with additional perforations 3 which are made cross-wise through the core 1 and coatings 2 to avoid hampering of the breathing of the skin pores after application thereof.

The strip in still plastic condition is rolled-up and cooled.

To be used, the strip and thus more particularly the core 1 is plasticized again by dipping the strip in a water bath of about 72° C.

The strip roll is taken out of the bath, it is left to drip for a few seconds, whereby the strip cools down to about 50° C. and the excess water is pressed out of the roll. The required amount of strip is unwound from the roll and it is laid to replace a plaster bandage, around a part of the body.

EXAMPLE 2

The composite material is manufactured in the same way as in example 1, but inside the second extruder, the core 1 from the thermoplastic composition is extruded in the shape of a plate with a thickness between 1 and 10 mm.

The core 1 is coated on either side with a coating 2 of unperforated polyester polyurethane foam with 0.6 mm thickness.

The resulting composite material in the form of a plate is particularly suitable to be used as splint which is brought to the required shape in soft condition.

To plasticize this composite material, it is heated to 70° to 150° C. e.g. approximately 80° C. during about 1 to 5 minutes depending on thickness inside an oven, on a hot plate or with hot air.

Shortly after heating is stopped, the temperature of core 1 drops down to about 60° C., whereafter the temperature drops quite slowly. Due to the plastic, the composite material even with this temperature of 60° C.

of the core, may be applied without any problem to the skin. The composite material provides a comfortable warmth and may be laid even on the most tender parts of the body.

In the form of embodiment shown in FIG. 3, the core 1 is comprised of three layers instead of one: a middle layer 11 and two outer layers 12 and 13.

All layers 11, 12 and 13 are from the thermoplastic composition mentioned herebefore, but the middle layer 11 has a lower caprolactone content and therefore a higher weakening point and a higher viscosity when heated than the outer layers 12 and 13. At the limit the outer layers 12 and 13 may consist of 100% polycaprolactone.

The fact that outer layers 12 and 13 have a lower weakening point results in the thermoplastic material of these relatively thin outer layers weakening more rapidly and having more rapidly a low viscosity when the composite material is heated up than when the whole core 1 has to be weakened. The thermoplastic material of these outer layers 12 and 13 is already able to traverse the foam coatings 2 when the middle layer 11 is still too rigid.

Not only the warming up time is shorter, but the expansion of the composite material due to heating up is also presented in the shape of a roll. Due to the expansion of the whole core 1 the successive windings would be pressed together and possibly stick to each other.

The composite material is manufactured in the same manner as in the previous described form of embodiment except that now each of the layers in the core 1 is prepared in the same way as the core 1 is prepared in the previous form of embodiment and the three layer core 1 is formed by co-extrusion.

The middle layer of the core 1 may comprise 1 to 40 weight % of microspheres of non-metallic heat accumulating material. Particular suitable materials are ceramics, more particularly glass. The microspheres have a diameter between 50 micrometer and 800 micrometer, preferably about 140 micrometer. Such glass microspheres reduce costs. Moreover, the microspheres increase the hardness of the layer 11 in cold condition. Strength of the layer is improved and the layer 11 may be thinner also reducing costs.

A very important advantage of the microspheres is that due to their heat-accumulation, the cooling of the core 1 is much slower so that the time for applying the composite material on the body is much increased.

The microspheres have also the supplemental advantage to clean the corresponding extruder.

Especially when warmed-up in a micro-wave oven the microspheres are heated and accumulate the heat. The heat is irradiated to the outer layers of the cored which become quickly enough soft and nearly liquid to traverse the foam layers when portions of the composite materials are pressed together. When weakened or heated-up the thermoplastic material is transparent. In cold and hard condition it is rather opaque. It is therefore useful to add a coloring material to the middle layer 11 of the core 1. As soon as the outer layers 12 and 13 have been sufficiently weakened to permit adhesion, they are transparent and the color of the middle layer 11 which is not yet weakened and not transparent will become visible through the very thin foam coating 2.

As long as the color of layer 11 is visible the core 1 is not yet completely hardened. So it is possible to see when the composite material is completely cooled off. Warming up of the composite material, especially when it is in the shape of a roll, can quickly be performed in a micro-wave oven.

The form of embodiment shown in FIG. 3 will be illustrated more in detail by following examples.

EXAMPLES 3 TO 6

A three layer core 1 is co-extruded with on the outer sides a layer of soft open cell polyurethane. The middle layer of the core is a mixture of 40 weight % polycaprolactone and 60 weight % of polycaprolactone polyester polyurethane to which are added glass microspheres and a coloring agent.

The outer layers do no have a coloring agent or glass microspheres. They consist of a mixture of 50 weight % polycaprolactone and 50 weight % polycaprolactone polyester polyurethane.

EXAMPLE 3 middle layer: 1 weight % glass microspheres with a diameter of 20 micrometer are added thickness: 0.2 mm.
outer layers: thickness: 0.1 mm.
foam coatings: thickness: 0.1 mm.
total thickness of composite layer: 0.5 mm.
heating time in a micro-wave oven of 600 W: 1.2 minutes
shape: strip or roll.
open time for applying the material: 10 minutes.

EXAMPLE 4

Same as Example 3 but microspheres have a diameter of 150 micrometer. The necessary heating time was 1.5 minutes.

EXAMPLE 5 middle layer: 40 wt % glass microspheres with a diameter of 800 micrometer.
thickness: 20 mm.
outer layers: thickness: 9 mm.
foam coatings: thickness: 1.4 mm.

EXAMPLE 6 middle layer: 20 wt % glass microspheres with a diameter of 140 micrometer, thickness: 2 mm.
outer layers: thickness: 0.9 mm.
foam coatings: thickness: 0.1 mm.
shape: strips, roles or plates.

The above-described composite material may be used in a lot of applications. The arrangement or applying thereof is quite easy. Portions from the material simply put on one another in plastic condition, do not stick or stick very slightly to one another, and it is but when such portions are pressed together that a fastening is obtained which, after becoming rigid, is very strong. As long as such cooling has not occurred, the portions may still be loosened from one another.

The composite material is also very temperature resistant. Even should the material be excessively heated, for example to 150° C. during thirty minutes, which is not excluded as heating occurs preferably not in a water bath but inside an oven, on a hot plate or in a hot air stream, the composite material does not lose in any way the properties thereof. It is only necessary to wait somewhat longer before the composite material can be used.

The foam plastic is so thin that it does not accumulate dust or dirt. If necessary it can be cleaned with a brush. The coatings prevent portions of the material undesirably sticking to each other or to the hands.

Thicker foam layers would prevent adhering together of overlapping portions of the composite material as the weakened thermoplastic core material would not be able to traverse the foam layers.

The coatings 2 from foam plastic also insure anti-slip properties. Once a bandage or splint from said composite material has been laid on the body, the foam plastic opposes the sliding of the bandage or splint. This is mostly of importance when for example, the material is arranged on moving limbs such as a foot for example.

The invention is in no way limited to the above-described embodiments and within the scope of the described embodiments, many changes may be brought notably as regards the composition, the imparted shapes, the size and the applications.

I claim:

1. A multi-layer composite material for medial or paramedical use, particularly orthopaedic, which comprises a multi-layer core having two sides with a thickness between 0.05 and 25 mm and on both sides of said multi-layer core a layer of soft non-thermoplastic resilient open cell foam plastic with a thickness outside the core between 0.05 and 1.5 mm, said core being comprised of three layers: a middle layer of a thermoplastic composition containing 20 to 70 weight % polyurethane and 80 to 30 weight % polycaprolactone and two outer layers containing a higher polycaprolactone content and having a lower weakening point than said middle layer.

2. The composite material of claim 1, wherein the outer layers of said core are comprised of pure polycaprolactone.

3. The composite material of claim 1, wherein the outer layers of said core are comprised of a higher polycaprolactone content than the middle layer, the remainder being a polyurethane.

4. The composite material of claim 1, wherein the outer layers of said core have a weakening point lower than the weakening point of the middle layer, each outer layer of said core having a thickness of about half the thickness of the middle layer.

5. The composite material of claim 1, in which the thermoplastic composition of the middle layer of said core contains 20 to 70 weight % caprolactone polyester polyurethane and 80 to 30 weight % polycaprolactone.

6. The composite material of claim 1, in which the layer of soft foam plastic is a layer of polyurethane foam.

7. The composite material of claim 1, in which the layer with the lowest polycaprolactone content of said core comprises a coloring agent.

8. A multi-layer composite material for medical or paramedical use, particularly orthopaedic, which comprises a core layer having two sides with a thickness between 0.05 and 25 mm of a thermoplastic composition containing 20 to 70 weight % polyurethane and 80 to 30 weight % polycaprolactone and on both sides of said core layer a layer of a soft non-thermoplastic resilient open-cell foam plastic with a thickness outside of the core between 0.05 to 1.5 mm, said core comprising 1 to 40 weight % of microspheres of non-metallic, heat-accumulating material with a diameter between 20 and 800 micrometers.

9. The composite material of claim 8, in which said core layer comprises about 20 weight % of microspheres of non-metallic, heat-accumulating material.

10. The composite material of claim 8, in which said core material comprises 1 to 40 weight % of glass microspheres.

11. A multi-layer composite material for medical or paramedical use, particularly orthopaedic, which comprises a core layer having two sides with a thickness between 0.05 and 25 mm of a thermoplastic composition containing 20 to 70 weight % polyurethane and 80 to 30 weight % polycaprolactone and on both sides of said core layer a layer of a soft non-thermoplastic resilient open-cell foam plastic with a thickness outside of the core between 0.05 to 1.5 mm, said core layer being comprised of three layers with different weakening points, the outer layers at the side of the soft foam plastic having a lower weakening point than the middle layer, said middle layer of the core comprising 1 to 40 weight % microspheres of non-metallic, heat-accumulating material.

12. A multi-layer composite material for medical or paramedical use, particularly orthopaedic, which comprises a core layer having two sides with a thickness between 0.05 and 25 mm of a thermoplastic composition containing 20 to 70 weight % polyurethane and 80 to 30 weight % polycaprolactone and on both sides of said core layer a layer of a soft non-thermoplastic resilient open-cell foam plastic with a thickness outside of the core between 0.05 to 1.5 mm, said core layer being comprised of three layers, the outer layers at the side of the soft foam plastic having a lower weakening point than the middle layer, said middle layer comprising 1 to 40 weight % of microspheres of non-metallic, heat-accumulating material, and a coloring agent.

* * * * *